US009376505B2

(12) United States Patent  
Geisser et al.

(10) Patent No.: US 9,376,505 B2  
(45) Date of Patent: *Jun. 28, 2016

(54) AQUEOUS IRON CARBOHYDRATE COMPLEXES, THEIR PRODUCTION AND MEDICAMENTS CONTAINING THEM

(75) Inventors: Peter Geisser, St. Gallen (CH); Erik Philipp, Arbon (CH); Walter Richle, Gossau (CH)

(73) Assignee: VIFOR (INTERNATIONAL) AG., St. Gallen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/556,733

(22) Filed: Jul. 24, 2012

(65) Prior Publication Data

US 2012/0316133 A1 Dec. 13, 2012

Related U.S. Application Data

(60) Continuation of application No. 12/581,212, filed on Oct. 19, 2009, now abandoned, which is a division of application No. 10/531,895, filed as application No. PCT/EP03/11596 on Oct. 20, 2003, now Pat. No. 7,612,109.

(30) Foreign Application Priority Data

Oct. 23, 2002 (DE) .................................. 102 49 552

(51) Int. Cl.

| | |
|---|---|
| A61K 31/295 | (2006.01) |
| A61K 31/78 | (2006.01) |
| A61K 33/26 | (2006.01) |
| A61K 47/36 | (2006.01) |
| C08B 37/00 | (2006.01) |
| A61K 31/718 | (2006.01) |
| A61K 45/06 | (2006.01) |
| A61K 47/48 | (2006.01) |
| C08B 30/18 | (2006.01) |
| C08B 31/18 | (2006.01) |

(52) U.S. Cl.

CPC ........... *C08B 37/0009* (2013.01); *A61K 31/295* (2013.01); *A61K 31/718* (2013.01); *A61K 33/26* (2013.01); *A61K 45/06* (2013.01); *A61K 47/4823* (2013.01); *C08B 30/18* (2013.01); *C08B 31/185* (2013.01); *Y10S 514/814* (2013.01)

(58) Field of Classification Search

CPC ... A61K 31/295; A61K 31/718; A61K 33/26; A61K 47/4823; C08B 37/0009; C08B 30/18; C08B 31/185

USPC .............. 514/502, 58, 59, 777, 814

See application file for complete search history.

(56) References Cited

U.S. PATENT DOCUMENTS

| | | |
|---|---|---|
| 1,129,307 A | 2/1915 | Marsh |
| 3,076,798 A | 2/1963 | Mueller et al. |
| 3,086,009 A | 4/1963 | Zuschek et al. |
| 3,324,109 A | 6/1967 | Eichel et al. |
| 3,574,184 A | 4/1971 | Alsop et al. |
| 3,591,616 A | 7/1971 | Baldt |
| 3,592,889 A | 7/1971 | Lindvall et al. |
| 3,821,192 A | 6/1974 | Montgomery et al. |
| 3,908,004 A | 9/1975 | Kitching |
| 4,180,567 A | 12/1979 | Herb |
| 4,370,476 A | 1/1983 | Usher et al. |
| 4,599,405 A | 7/1986 | Muller et al. |
| 4,788,281 A | 11/1988 | Tosoni et al. |
| 5,160,726 A | 11/1992 | Josephson et al. |
| 5,624,668 A | 4/1997 | Lawrence et al. |
| 5,746,999 A | 5/1998 | Gries et al. |
| 5,756,715 A | 5/1998 | Monte et al. |
| 5,831,043 A | 11/1998 | Fleche |
| 5,866,533 A | 2/1999 | Beck et al. |
| 6,773,924 B2 | 8/2004 | Beck et al. |
| 6,911,342 B2 | 6/2005 | Helenek et al. |
| 6,960,571 B2 | 11/2005 | Helenek et al. |
| 7,169,359 B2 | 1/2007 | Helenek et al. |
| 7,612,109 B2 * | 11/2009 | Geisser et al. ............... 514/502 |
| 7,687,273 B2 | 3/2010 | Beck et al. |
| 7,754,702 B2 * | 7/2010 | Helenek et al. ............. 514/54 |
| 7,883,897 B2 | 2/2011 | Beck et al. |
| 7,964,568 B2 | 6/2011 | Beck et al. |

(Continued)

FOREIGN PATENT DOCUMENTS

| | | |
|---|---|---|
| CN | 1353194 A | 6/2002 |
| CZ | 245379 | 12/1983 |

(Continued)

OTHER PUBLICATIONS

Product Information of Ferinject for Australia (2011).  
CAS Registry Handbook(R2) 2025R-4072R (1965-1971)—Chemical Abstracts Service Registry Handbook Number Section.  
Singh et al., "A Comparison Between Intravenous Iron Polymaltose Complex (Ferrum Hausmann) and Oral Ferrous Fumarate in the Treatment of Iron Deficiency Anaemia in Pregnancy", *Eur. J. Haematology*, vol. 60, pp. 119-124 (1998).

(Continued)

*Primary Examiner* — John Pak  
(74) *Attorney, Agent, or Firm* — Polsinelli PC

(57) ABSTRACT

A water soluble iron carbohydrate complex obtainable from an aqueous solution of iron(III) salt and an aqueous solution of the oxidation product of one or more maltrodextrins using an aqueous hypochlorite solution at a pH-value within the alkaline range, where, when one maltodextrin is applied, its dextrose equivalent lies between 5 and 20, and when a mixture of several maltodextrins is applied, the dextrose equivalent of the mixture lies between 5 and 20 and the dextrose equivalent of each individual maltodextrin contained in the mixture lies between 2 and 40, a process for its production and a medicament for the treatment and prophylaxis of iron deficiency conditions.

36 Claims, No Drawings

(56) References Cited

U.S. PATENT DOCUMENTS

| | | | | |
|---|---|---|---|---|
| 8,263,577 | B2* | 9/2012 | Reim et al. | 514/54 |
| 8,722,101 | B2* | 5/2014 | Tanner-Baumgartner et al. | 424/647 |
| 8,895,612 | B2* | 11/2014 | Helenek et al. | 514/502 |
| 2006/0116349 | A1 | 6/2006 | Helenek et al. | |
| 2007/0161600 | A1 | 7/2007 | Helenek et al. | |
| 2008/0214496 | A1 | 9/2008 | Tanner-Baumgartner et al. | |
| 2008/0234226 | A1 | 9/2008 | Erichsen et al. | |
| 2008/0269167 | A1 | 10/2008 | Ziegler et al. | |
| 2010/0099647 | A1 | 4/2010 | Geisser et al. | |

FOREIGN PATENT DOCUMENTS

| | | |
|---|---|---|
| DE | 461 370 C | 6/1928 |
| DE | 3 443 251 A1 | 5/1986 |
| DE | 696 15 620 T2 | 4/2002 |
| DE | 102 49 552 A1 | 5/2004 |
| EP | 0150085 A2 | 7/1985 |
| EP | 0 755 944 A2 | 1/1997 |
| EP | 0 875 249 A1 | 11/1998 |
| EP | 1 719 496 A2 | 11/2006 |
| FR | 1 451 203 | 1/1966 |
| GB | 828404 A | 2/1960 |
| GB | 879441 A | 10/1961 |
| GB | 928238 A | 6/1963 |
| GB | 978485 A | 12/1964 |
| GB | 1 111 929 | 5/1968 |
| GB | 1199951 A | 7/1970 |
| GB | 1258566 A | 12/1971 |
| GB | 1377006 A | 12/1974 |
| GB | 2 129 821 A | 5/1984 |
| WO | WO-95/32978 A1 | 12/1995 |
| WO | WO-97/17377 A1 | 5/1997 |
| WO | WO-00/30657 A1 | 6/2000 |
| WO | WO-00/66634 A1 | 11/2000 |
| WO | WO-02/46241 | 6/2002 |
| WO | WO-2004/019032 A1 | 3/2004 |
| WO | WO-2004/082693 A1 | 9/2004 |
| WO | WO-2006/084782 A1 | 8/2006 |
| WO | WO-2007/023154 A2 | 3/2007 |
| WO | WO-2007/055804 A2 | 5/2007 |
| WO | WO-2007/060038 A2 | 5/2007 |
| WO | WO-2007/081744 A2 | 7/2007 |

OTHER PUBLICATIONS

Besemer, A.C., et al., "The Relation between Calcium Sequestering Capacity and Oxidation Degree of Dicarboxy-Starch and Dicarboxy-Inulin", Starke-Starch, vol. 46, No. 11, (1994), pp. 419-422.
De Nooy, A.E.J., et al., "On the Use of Stable Organic Nitroxyl Radicals for the Oxidation of Primary and Secondary Alcohols", Synthesis, vol. 10, (1996), pp. 1153-1174.
Besemer, A. C., et al., "Dicarboxy-starch by Sodium Hypochlorite Bromide Oxidation and Its Calcium Binding Properties", Starch/Stärke, vol. 46, No. 3, (1994), pp. 95-101.
Besemer, A.C., et al., "The Hypochlorite Oxidation of Inulin", Recueil Travaux Chim Pays-Bas, vol. 113, No. 9, (1994), pp. 398-402.
Besemer, A.C., et al., "The Catalytic Effect of Bromide in the Hypochlorite Oxidation of Linear Dextrins and Inulin", Starch/Stärke, vol. 46, No. 3, (1994), pp. 101-106.
Deary, M.E., et al., "Evidence for Cyclodextrin Dioxiranes", Carbohydrate Research, vol. 309, (1998), pp. 17-29.
Kardos, N., et al., "Sonochemistry of Carbohydrate Compounds", Carbohydrate Research, vol. 332, (2001), pp. 115-131.
Anelli, P.L., et al., "Fast and Selective Oxidation of Primary Alcohols to Aldehydes or to Carboxylic Acids and of Secondary Alcohols to Ketones Mediated by Oxammonium Salts Under Two-Phase Conditions", J. of Organic Chemistry, vol. 52, (1987), pp. 2559-2562.
Dextran Structure, http://www.dextran.net/dextran-structure.html.
De Belder, A.N., "Dextran" Dextran Handbook (Amersham) (2003), pp. 1-64.

Rote Liste, product information for Ferrum Hausmann (1996).
Auerbach, M., et al., "Clinical Use of Intravenous Iron: Administration, Efficacy, and Safety, Hematology", (2010), pp. 338-347.
Bailie, G., "Breaking New Ground in Intravenous Iron Therapy", European Haematology, (2008), pp. 58-60.
Bolivian Marketing approval for Ferrum Hausmann (dated 1960).
Ferinject: Product label in Europe.
German Marketing approval for Ferrum Hausmann (dated 1978).
"International Nonproprietary Names for Pharmaceutical Substnaces (INN)", World Health Organization, vol. 22, No. 1, (2008), pp. 41-42, 54.
Römpp encyclopedia chemistry 9 ("Römpp Chemie Lexikon"); 10th edition, vol. 2, Cm-G, p. 213, 1997, catchword "dextrin".
Römpp encyclopedia chemistry 9 ("Römpp Chemie Lexikon"); 10th edition, vol. 4, M-Pk, p. 518, 1998, catchword "maltodextrin".
Bailie, G.R., "Efficacy and Safety of Ferric Carboxymaltose in Correcting Iron-Deficiency Anemia: A Review of Randomized Controlled Trials across Different Indications", Arzneimittelforschung, vol. 60, No. 6a), (2010), pp. 386-398.
Burckhardt-Herold, S., et al., "Interactions Between Iron (III)-hydroxide Polymaltose Complex and Commonly Used Drugs", Arzneimittel-Forschung, vol. 57, No. 6a, (2007), pp. 360-369.
Burger, K., et al., "A Novel Plynuclear Iron(III) Mixed Ligand Complex for Use in Parenteral Iron Therapy", Inorganica Chimica Acta, vol. 80, (1983), pp. 231-235.
Coe, E., et al., "Comparison of Polysaccharide Iron Complexes Used as Iron Supplements", Journal of Inorganic Biochemistry, vol. 57, (1995), pp. 287-292.
Devaki, P. B., et al., "Effects of Oral Iron (III) Hydroxide Polymaltose Complex Supplementation of Hemoglobin Increase, Cognitive Function, Affective Behavior and Scholastic Performance of Adolescents with Varying Iron Status", Arzneimittel-Forschung, vol. 59, No. 6, (2009), pp. 303-310.
Driss, F., et al., "Effects of Intravenous Polymaltose Iron on Oxidant Stress and Non-Transferrin-Bound Iron in Hemodialysis Patients", Nephron Clinical Practice, (2005), vol. 99, pp. 63-67.
European Search Report EP 10 194 332.2, Jan. 12, 2011. (See Translation).
Ferrlecit NDA 20-955 Ferrlecit, (1999), pp. 1-10.
Ferrlecit 62,5, Beipackzettel Packungsbellage & Fachinformation, (2011), pp. 1-5. (German).
Funk, F., et al., "Interactions Between Iron (III)-hydroxide Polymaltose Complex and Commonly Used Medications", Arzneimittel-Forschung (Drug Research), vol. 57, No. 6a, (2007), pp. 370-375.
Geetha, K., et al., "Transition-Metal Saccharide Chemistry: Synthesis, Spectroscopy, Electrochemistry and Magnetic Susceptibility Studies of Iron (III) Complexes of Mono- and Disaccharides", Carbohydrate Research, vol. 271, (1995), pp. 163-175.
Geisser, P., et al., "Structure/Histotoxicity Relationship of Parenteral Iron Preparations", Arzneim.-Forsch/Drug Res., vol. 42 (ii), No. 12, (1992), pp. 1439-1452.
Geisser, P., "Safety and Efficacy of Iron (III)—hydroxide Polymaltose Complex", Arzneimittel-Forschung (Drug Research), vol. 57, No. 6a, (2007), pp. 439-452.
Kearsley, M. W., et al., "The Determination of the Iron/Chelating Abilithy of Different Carbohydrates and the Preparation of Ferric/Carbohydrate Complexes", Acia Alimentaria, vol. 8, No. 1, (1979), pp. 69-78.
Lange, W. E., et al., "Avalability of Ionic Iron from Iron Chelates", J. Pharmac. Sci., vol. 51, (1962), pp. 1128-1131.
Lundqvist, H., et al., "Food Interaction of Oral Uptake of Iron", Arzneimittel-Forschung (Drug Research), vol. 57, No. 6a, (2007), pp. 401-416.
MacDougall, I. C., "Evolution of IV Iron Compounds over The Last Centruy", Journal of Renal Care, vol. 35 (s2), (2009), pp. 8-13.
Mannich, C., et al., "Ueber die kolloide Natur des Eisenzuckers", (1922), p. 158-166.
Mannich, V.C., et al., "Wissenschaftliche Mitteilungen", Apotheker-Zeitung, No. 37, (1913), pp. 329-330. (German) See translation.
Mannich, V.C., et al., "Wissenschaftliche Mitteilungen", Apotheker-Zeitung, No. 37, (1913), pp. 329-330. Machine translation.

(56) References Cited

OTHER PUBLICATIONS

Picaud, J. C., et al., "Supplémentation en fer chez les enfants prématurés traités par érythropoïétine", Arch Pediatr, vol. 6, (1999), pp. 657-664.

Pugh-Clarke, K., et al., "An Evidence-Based Approach to Anaemia Management in Predialysis Chronic Kidney Disease", Journal of Renal Care, vol. 35 (s2), (2009), pp. 29-31.

Qunibi, W. Y., "The Efficacy and Safety of Current Intravenous Iron Preparations for the Management of Iron-Deficiency Anaemia: A Review", Arzneimittelforschung, vol. 60, No. 6a, (2010), pp. 399-412.

Ranfaing, E., "Treatments of the Martial Deficiencies: Preparations Available in France", Néphrologie & Thérapeutique, vol. 5, (2006), pp. 5337-5340. (Abstract).

Rao, C. P., et al., "Fe (III) Complexes of D-glucose and D-Fructose", BioMetals, vol. 7, (1994), pp. 25-29.

Rao, C. P., et al., "Solution Stability of Iron-Saccharide Complexes", Bioorganic & Medicinal Chemistry Letters, vol. 2, No. 9, (1992), pp. 997-1002.

Rao, C. P., et al., "Transition Metal Saccharide Chemistry and Biology: Syntheses, Characterization, Solution Stability and Putative Bio-Relevant Studies of Iron-Saccharide Complexes", Inorganica Chimica Acta, vol. 297, (2000), pp. 373-382.

Tagboto, S., et al., "The Efficacy of a Single Dose of Intravenous Ferric Carboxymaltose (Ferinject®) On Anaemia in a Pre-Dialysis Population of Chronic Kideny Disease Patients", Journal of Renal Care, (2009), vol. 35, No. 1, pp. 18-22.

Tonkovic, M., et al., "Preparation and Properties of FE(III)-Sugar Complexes", Inorganica Chimica Acta, vol. 80, (1983), pp. 251-254.

Venofer Label, American Regent, Inc. Shirley, NY 11967.

English translation of CN 1353194 (Jun. 12, 2002), ten pages.

Dokic et al., "Molecular Characteristics of Maltodextrins and Rheological Behaviour of Diluted and Concentrated Solutions", Colloids Surfaces A: Physicochem. Eng. Aspects, vol. 141, (1998), pp. 435-440.

Thaburet et al., "TEMPO-mediated Oxidation of Maltodextrins and D-glucose: Effect of pH on the Selectivity and Sequestering Ability of the Resulting Polycarboxylates", Carbohydrate Research, vol. 330, (2001), pp. 21-29.

International Search Report for corresponding PCT/EP2003/11596 mailed Jan. 23, 2004, 3 pages.

HCAPLUS Abstract 1960:117732 (1960), one page.

HCAPLUS Abstract 2003:135397 (2003), one pages.

Machine English translation of FR 1 451 203 (Jan. 7, 1966), six pages.

English translation of CZ 245379 B1 (Jan. 16, 1986), eight pages.

Ferrlecit Highlights of Prescribing Information (Aug. 2011).

\* cited by examiner

AQUEOUS IRON CARBOHYDRATE COMPLEXES, THEIR PRODUCTION AND MEDICAMENTS CONTAINING THEM

RELATED APPLICATIONS

This application is a continuation of U.S. application Ser. No. 12/581,212, filed Oct. 19, 2009, which is incorporated by reference in its entirety herein and which is a division of U.S. application Ser. No. 10/531,895, filed Dec. 14, 2005, which issued as U.S. Pat. No. 7,612,109 on Nov. 3, 2009 and which is a national stage application under 35 U.S.C. §371 of PCT/EP2003/011596, filed Oct. 20, 2003, which claims benefit of German application 102 49 552.1, filed Oct. 23, 2002.

BACKGROUND OF THE INVENTION

Iron deficiency anemia can be treated or prophylactically treated by the application of medicaments containing iron. In this respect the use of iron carbohydrate complexes is known. A water soluble iron (III) hydroxide sucrose complex is a frequently and successfully used preparation (Danielson, Salmonson, Derendorf, Geisser, Drug Res., Vol. 46: 615-621, 1996). It is also known in the art to use, for parenteral application, iron dextran complexes as well as complexes based on pullulans (WO 02/46241), which are difficult to obtain and have to be produced under pressure at high temperatures and involving hydrogenating steps. Other iron carbohydrate complexes are also known for oral application.

BRIEF SUMMARY OF THE INVENTION

The present invention concerns water-soluble iron carbohydrate complexes which are used for the treatment of iron deficiency anemia, their preparation, medicaments containing them and their use for the prophylaxis or treatment of iron deficiency anemia. The medicaments are especially useful for parenteral application.

DETAILED DESCRIPTION OF THE INVENTION

The problem to be solved by the present invention is to provide an iron preparation which is especially to be applied parenterally and which can easily be sterilized; the known parenterally applicable preparations on the basis of sucrose and dextran were only stable at temperatures up to 100° C., which made sterilization difficult. Further, the preparation to be provided by the invention shall have reduced toxicity and shall avoid dangerous anaphylactic shocks which can be induced by dextran. Also, the stability of the complexes of the preparation shall be high in order to enable a high applicable dosage and a high rate of application. Furthermore, the iron preparation is to be producible from easily obtainable starting products and without great effort.

In accordance with the present invention the problem can be solved by providing iron (III) carbohydrate complexes on the basis of the oxidation products of maltodextrins. Therefore, an object of the present invention is water soluble iron carbohydrate complexes, which are obtainable from an aqueous solution of an iron (III) salt and an aqueous solution of the oxidation product of one or more maltodextrins, using an aqueous hypochlorite solution at an alkaline pH value, e.g., of 8 to 12 where, when one maltodextrin is applied, its dextrose equivalent lies between 5 and 20, and when a mixture of several maltodextrins is applied, the dextrose equivalent of the mixture lies between 5 and 20 and the dextrose equivalent of each individual maltodextrin contained in the mixture lies between 2 and 40.

A further object of the present invention is a process for producing the iron carbohydrate complexes according to the invention wherein one or more maltodextrins are oxidized in an aqueous solution at an alkaline pH value, e.g., of 8 to 12 using an aqueous hypochlorite solution and reacting the obtained solution with an aqueous solution of an iron (III) salt where, when one maltodextrin is applied, its dextrose equivalent lies between 5 and 20, and when a mixture of several maltodextrins is applied, the dextrose equivalent of the mixture lies between 5 and 20 and the dextrose equivalent of each individual maltodextrin contained in the mixture lies between 2 and 40.

The usable maltodextrins are easily obtainable starting products, and they are commercially available.

In order to prepare the ligands of the complexes of the invention, the maltodextrins are oxidized in an aqueous solution with a hypochlorite solution. Suitable examples are solutions of alkali hypochlorites such as a solution of sodium hypochlorite. Commercially available solutions can be used. The concentration of the hypochlorite solution, e.g., is at least 13% by weight, preferably on the order of 13 to 16% by weight, calculated as active chlorine. Preferably the solutions are used in such an amount that about 80 to 100%, preferably about 90%, of one aldehyde group per molecule of maltodextrin is oxidized. In this manner, the reactivity caused by the glucose content of the maltodextrin molecules is lowered to 20% or less, preferably to 10% or less.

The oxidation is carried out in an alkaline solution, e.g., at a pH of 8 to 12, for example 9 to 11. As an example, oxidation can be carried out at temperatures on the order of 15 to 40° C., preferably of 25 to 35° C. The reaction times are, e.g, on the order of 10 minutes to 4 hours, e.g., 1 to 1.5 hours.

By this procedure the degree of depolymerization of the starting maltodextrins is kept at a minimum. Only theoretically it is assumed that the oxidation occurs mainly at the terminal aldehyde group (acetal or semiacetal group, respectively) of the maltodextrin molecules.

It is also possible to catalyze the oxidation reaction of the maltodextrins. The addition of bromide ions is suitable, e.g., in the form of alkali bromides, for example sodium bromide. The added amount of bromide is not critical. The amount is kept as low as possible in order to achieve an end product (Fe-complex) which can easily be purified. Catalytic amounts are sufficient. As stated above, the addition of bromide is possible, however, not necessary.

Further, it is also possible to use other oxidation systems, such as, e.g., the known ternary oxidation system hypochlorite/alkali bromide/2,2,6,6-tetramethylpiperidine-1-oxyl (TEMPO) for the oxidation of the maltodextrins. The process to oxidize maltodextrins catalytically with alkali bromides or with the ternary TEMPO system is described, e.g., by Thaburet et al, in Carbohydrate Research 330 (2001) 21-29, which method can be used for the present invention, In order to prepare the complexes of the invention, the obtained oxidized maltodextrins are reacted with an iron (III) salt in an aqueous solution. In order to do so, the oxidized maltodextrins can be isolated and redissolved. It is also possible, however, to use the obtained aqueous solutions of the oxidized maltodextrins directly for the further reaction with the aqueous iron (III) solutions.

Water soluble salts of inorganic or organic acids, or mixtures thereof, such as halides, e.g., chloride and bromide, or sulfates can be used as iron (III) salts. It is preferred to use physiologically acceptable salts. It is especially preferred to use an aqueous solution of iron (III) chloride.

It has been found that the presence of chloride ions favors the formation of the complexes. The chloride ions can be used in the form of water soluble chlorides such as alkali metal chlorides, e.g., sodium chloride, potassium chloride or ammonium chloride. As stated, the iron (III) is preferably used in the form of the chloride.

For instance, the aqueous solution of the oxidized maltodextrin can be mixed with an aqueous solution of the iron (III) salt in order to carry out the reaction. Here, it is preferred to proceed in a manner so that during and immediately after mixing the oxidized maltodextrin and the iron (III) salt, the pH is strongly acid or so low that no hydrolysis of the iron (III) salt occurs, e.g., pH 2 or less, in order to avoid an undesired precipitation of iron hydroxides. In general, it is not necessary to add an acid, if iron (III) chloride is used, since aqueous solutions of iron (III) chloride can be sufficiently acidic. Only after mixing, the pH is raised to values, e.g., on the order of at least 5, for example, up to 11, 12, 13 or 14. The pH is preferably raised slowly or gradually which, for example, can be achieved by first adding a weak base, for example, up to a pH of about 3, and then neutralizing further using a stronger base. Examples of weak bases are alkali—or alkaline earth—carbonates, bicarbonates, such as sodium and potassium carbonate or bicarbonate, or ammonia. Examples of strong bases are alkali—or alkaline earth—hydroxides such as sodium, potassium, calcium or magnesium hydroxide.

The reaction can be improved by heating. For example, temperatures on the order of 15° C. up to boiling point can be used. It is preferred to raise the temperature gradually. Thus, for example, it is possible to heat to about 15 to 70° C. and then raise the temperature gradually up to boiling point.

The reaction times are, for example, on the order of 15 minutes up to several hours, e.g., 20 minutes to 4 hours, such as 25 to 70 minutes, e.g., 30 to 60 minutes.

The reaction can be carried out in a weakly acid range, for example, at a pH on the order of 5 to 6. However, it has been found, that it is useful, but not necessary, to raise the pH during the formation of the complexes to higher values of up to 11, 12, 13 or 14. In order to complete the reaction, the pH can be lowered then by addition of an acid, for example, to the order of 5 to 6. It is possible to use inorganic or organic acids or a mixture thereof, especially hydrogen halide acids such as hydrogen chloride or aqueous hydrochloric acid, respectively.

As stated above, the formation of the complexes is usually improved by heating. Thus, at the preferred embodiment of the invention, wherein the pH is raised during the reaction to ranges of at least 5 and above, up to 11 or 14, it is, for instance, possible to work at first at lower temperatures on the order of 15 to 70° C., such as 40 to 60° C., e.g., about 50° C., whereafter the pH is reduced to values on the order of at least 5, and the temperature is gradually raised over 50° C. up to boiling point The reaction times are on the order of 15 minutes up to several hours and they can vary depending on the reaction temperature. If the process is carried out with an intermediate pH of more than 5, it is, for example, possible to work 15 to 70 minutes, e.g., 30 to 60 minutes, at the enhanced pH, for example, at temperatures of up to 70° C., whereafter the pH is lowered to a range on the order of at least 5 and the reaction is carried out for a further 15 to 70 minutes, e.g., 30 to 60 minutes, at temperatures, e.g., up to 70° C., and optionally a further 15 to 70 minutes, e.g., 30 to 60 minutes, at higher temperatures up to boiling point.

After the reaction the obtained solution can be cooled, e.g., to room temperature and can optionally be diluted and optionally be filtered. After cooling, the pH can be adjusted to the neutral point or a little below, for example, to values of 5 to 7, by the addition of an acid or base. It is possible to use, e.g., the acids and bases which have been mentioned for carrying out the reaction. The solutions obtained are purified and can directly be used for the production of medicaments. However, it is also possible to isolate the iron (III) complexes from the solution, e.g., by precipitation with an alcohol such as an alkanol, for example, ethanol. Isolation can also be effected by spray-drying. Purification can take place in the usual way, especially in order to remove salts. This can, for example, be carried out by reverse osmosis. It is, for example, possible to carry out the reverse osmosis before spray-drying or before a direct application in medicaments.

The iron content of the obtained iron (III) carbohydrate complexes is, for example, 10 to 40% weight/weight, especially, 20 to 35% weight/weight. They can easily be dissolved in water. It is possible to prepare neutral aqueous solutions which, e.g., have an iron content of 1% weight/vol. to 20% weight/vol. Such solutions can be sterilized thermally. The weight average molecular weight of the obtained complexes, is, for example, 80 kDa to 400 kDa, preferably 80 kDa to 350 kDa, especially preferred up to 300 kDa (measured by gel permeation chromatography, e.g., as described by Geisser et al, in Arzneim. Forsch/Drug Res. 42(11), 12, 1439-1452 (1992), paragraph 2.2.5).

As stated above, it is possible to provide aqueous solutions from the complexes of the invention. These solutions are especially useful for parenteral application. However, it is also possible to apply them orally or topically. Contrary to the known parenterally applicable iron preparations, they can be sterilized at high temperatures, e.g., at 121° C. and above, at short contact times of, e.g., 15 minutes, by acquiring $F_0 \geq 15$. The contact times are correspondingly shorter at higher temperatures. Preparations hitherto known had to be sterilely filtrated and mixed with preservatives, such as benzyl alcohol or phenol. Such additives are not necessary in the invention. Hence, it is possible to fill the solutions of the complexes, for example, into ampoules. It is, for example, possible to fill solutions having a content of 1 to 20% by weight, e.g., 5% by weight, into vessels such as ampoules or phials, e.g., of 2 to 100 ml, e.g., up to 50 ml. The preparation of the parenterally applicable solutions can be carried out as known in the art, optionally using additives which are normally used for parenteral solutions. The solutions can be formulated in such a way that they can be administered by injection or in the form of an infusion, e.g., in brine solution. For the oral or topical application it is possible to formulate preparations with usual excipients and additives.

Thus, a further object of the invention is aqueous medicaments which are especially useful for the parenteral, intravenous but also intramuscular application, as well as for oral or topical application. The aqueous medicaments are especially useful for the treatment of iron deficiency anemia. A further object of the invention is also the use of the iron (III) carbohydrate complexes according to the invention for the treatment and prophylaxis of iron deficiency anemia or the production of medicaments especially for the parenteral treatment of iron deficiency anemia. The medicaments can be used in human and veterinary medicine.

The advantages which are achieved with the iron (III) carbohydrate complexes of the invention are the above-mentioned high sterilization temperatures, as well as the low toxicity and the reduced danger of anaphylactic shock. The toxicity of the complexes according to the invention is very low. The $LD_{50}$ lies at over 2000 mg Fe/kg, compared to the $LD_{50}$ of the known pullulan complexes, which lies at 1400 mg Fe/kg. In view of the high stability of the complexes of the invention, it is possible to enhance the rates of application as well as the dosages. Thus, it is possible to apply the medicaments of the invention parenterally in the form of a single dose. Such a single dose is, for example, 500 to 1000 mg iron. The dose can be applied, for example, during the course of one hour. A further advantage lies in the high degree of availability of the maltodextrins used as starting products, which are, e.g., commercially available additives in the food processing industry.

In the present description, as well as in the following examples, the dextrose equivalents are measured gravimetrically. In order to do so, the maltodextrins are reacted in a boiling aqueous solution with Fehling's solution. The reaction is carried out quantitatively, i.e. until the Fehling's solution is no longer discolored. The precipitated copper (I) oxide is dried at 105° C. until a constant weight is achieved and measured gravimetrically. The glucose content (dextrose equivalent) is calculated from the obtained results as % weight/weight of the maltodextrin dry substance. It is, for example, possible to use the following solutions: 25 ml Fehling's solution I, mixed with 25 ml Fehling's solution II; 10 ml aqueous maltodextrin solution (10% mol/vol) (Fehling's solution I: 34.6 g copper (II) sulfate dissolved in 500 ml water; Fehling's solution II: 173 g potassium sodium tartrate and 50 g sodium hydroxide dissolved in 400 ml water).

Example 1

100 g maltodextrin (9.6 dextrose equivalent measured gravimetrically) are dissolved by stirring in 300 ml water at 25° C. and oxidized by addition of 30 g sodium hypochlorite solution (13 to 16 weight percent active chlorine) at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide, and the solution is heated to 50° C. and kept at 50° C. for 30 minutes. Then, acidification to a pH of 5 to 6 is effected by addition of hydrochloric acid, the solution is kept at 50° C. for a further 30 minutes and then heated to 97-98° C., and the temperature is kept for 30 minutes at this range. After cooling the solution to room temperature, the pH is adjusted to 6-7 by the addition of sodium hydroxide.

The solution is then filtered through a sterilization filter and then examined for sediments. Thereafter, the complex is isolated by precipitation with ethanol in a range of 1:0.85, and then dried in vacuum at 50° C.

The yield is 125 g (corresponding to 87% of the theoretical value) of a brown amorphous powder having an iron content of 29.3% weight/weight (measured complexometrically).

Molecular weight mw 271 kDa.

Example 2

200 g maltodextrin (9.6 dextrose equivalent measured gravimetrically) are dissolved by stirring in 300 ml water at 25° C. and oxidized by addition of 30 g sodium hypochlorite solution (13 to 16 weight percent active chlorine) at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide, and the solution is heated to 50° C. and kept for 30 minutes at 50° C. Then, acidification to a pH of 5 to 6 is effected by addition of hydrochloric acid, the solution is kept at 50° C. for a further 30 minutes and then heated to 97-98° C., and the temperature Is kept for 30 minutes at this range. After cooling the solution to room temperature, the pH is adjusted to 6-7 by the addition of sodium hydroxide.

The solution is then filtered through a sterilization filter and then examined for sediments. Thereafter, the complex is isolated by precipitation with ethanol in a range of 1:0.85, and then dried in vacuum at 50° C.

The yield is 123 g (corresponding to 65% of the theoretical value) of a brown amorphous powder having an iron content of 22.5% weight/weight (measured complexometrically).

Molecular weight mw 141 kDa,

Example 3

100 g maltodextrin (9.6 dextrose equivalent measured gravimetrically) are dissolved by stirring in 300 ml water at 25° C. and oxidized by addition of 30 g sodium hypochlorite solution (13 to 16 weight percent active chlorine) and 0.7 g sodium bromide at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 6.5 by addition of sodium hydroxide and the solution is heated to 50° C. and kept for 60 minutes at 50° C. Then, acidification to a pH of 5 to 6 is effected by addition of hydrochloric acid, the solution is kept at 50° C. for a further 30 minutes and then heated to 97-98° C., and the temperature is kept for 30 minutes at this range. After cooling the solution to room temperature the pH is adjusted to 6-7 by the addition of sodium hydroxide.

The solution is then filtered through a sterilization filter and then examined for sediments. Thereafter, the complex is isolated by precipitation with ethanol in a range of 1:0.85 and then dried in vacuum at 50° C.

The yield is 139 g. (corresponding to 88% of the theoretical value) of a brown amorphous powder having an iron content of 26.8% weight/weight (measured complexometrically).

Molecular weight mw 140 kDa.

Example 4

A mixture of 45 g maltodextrin (6.6 dextrose equivalent measured gravimetrically) and 45 g maltodextrin (14.0 dextrose equivalent measured gravimetrically) is dissolved by stirring in 300 ml water at 25° C. and oxidized by addition of 25 g sodium hypochlorite solution (13 to 16 weight percent active chlorine) and 0.6 g sodium bromide at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 30 minutes and then heated to 97-98° C., and the temperature is kept for 30 minutes at this range. After cooling the solution to room temperature the pH is adjusted to 6-7 by the addition of sodium hydroxide.

The solution is then filtered through a sterilization filter and then examined for sediments. Thereafter, the complex is isolated by precipitation with ethanol in a range of 1:0.85 and then dried in vacuum at 50° C., The yield is 143 g (corresponding to 90% of the theoretical value) of a brown amorphous powder having an iron content of 26.5% weight/weight (measured complexometrically).

Molecular weight mw 189 kDa,

Example 5

90 g maltodextrin (14.0 dextrose equivalent measured gravimetrically) are dissolved by stirring in 300 ml water at 25° C. and oxidized by addition of 35 g sodium hypochlorite solution (13 to 16 weight percent active chlorine) and 0.6 g sodium bromide at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 30 minutes and then heated to 97-98° C. and the temperature is kept for 30 minutes at this range. After cooling the solution to room temperature the pH is adjusted to 6-7 by the addition of sodium hydroxide.

The solution is then filtered through a sterilization filter and then examined for sediments. Thereafter, the complex is isolated by precipitation with ethanol in a range of 1:0.85 and then dried in vacuum at 50° C.

The yield is 131 g (corresponding to 93% of the theoretical value) of a brown amorphous powder having an iron content of 29.9% weight/weight (measured complexometrically).

Molecular weight mw 118 kDa.

Example 6

A mixture of 45 g maltodextrin (5.4 dextrose equivalent measured gravimetrically) and 45 g maltodextrin (18.1 dextrose equivalent measured gravimetrically) is dissolved by stirring in 300 ml water at 25° C. and oxidized by addition of 31 g sodium hypochlorite solution (13 to 16 weight percent active chlorine) and 0.7 g sodium bromide at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 30 minutes and then heated to 97-98° C. and the temperature is kept for 30 minutes at this range. After cooling the solution to room temperature the pH is adjusted to 6-7 by the addition of sodium hydroxide.

The solution is then filtered through a sterilization filter and then examined for sediments. Thereafter, the complex is isolated by precipitation with ethanol in a range of 1:0.85 and then dried in vacuum at 50° C.

The yield is 134 g (corresponding to 88% of the theoretical value) of a brown amorphous powder having an iron content of 27.9% weight/weight (measured complexometrically).

Molecular weight mw 178 kDa.

Example 7

100 g maltodextrin (9.6 dextrose equivalent measured gravimetrically) are dissolved by stirring in 300 ml water at 25° C. and oxidized by addition of 29 g sodium hypochlorite solution (13 to 16 weight percent active chlorine) and 0.7 g sodium bromide at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 70 minutes. After cooling the solution to room temperature the pH is adjusted to 6-7 by the addition of sodium hydroxide.

The solution is then filtered through a sterilization filter and then examined for sediments. Thereafter, the complex is isolated by precipitation with ethanol in a range of 1:0.85 and then dried in vacuum at 50° C.

The yield is 155 g (corresponding to 90% of the theoretical value) of a brown amorphous powder having an iron content of 24.5% weight/weight (measured complexometrically).

Molecular weight mw 137 kDa.

Example 8

126 g maltodextrin (6.6 dextrose equivalent measured gravimetrically) are dissolved by stirring in 300 ml water at 25° C. and oxidized by addition of 24 g sodium hypochlorite solution. (13 to 16 weight percent active chlorine) and 0.7 g sodium bromide at pH 10.

At first, the oxidized maltodextrin solution and then 554 g sodium carbonate solution (17.3% weight/weight) are added at room temperature to 352 g of a stirred iron (III) chloride solution (12% weight by weight Fe).

Then, the pH is adjusted to 11 by addition of sodium hydroxide and the solution is heated to 50° C. and kept for 30 minutes at 50° C. Then, acidification to a pH of 5 to 6 is effected by addition of hydrochloric acid, the solution is kept at 50° C. for a further 70 minutes. After cooling the solution to room temperature the pH is adjusted to 6-7 by the addition of sodium hydroxide.

The solution is then filtered through a sterilization filter and then examined for sediments. Thereafter, the complex is isolated by precipitation with ethanol in a range of 1:0.85 and then dried in vacuum at 50° C.

The yield is 171 g (corresponding to 86% of the theoretical value) of a brown amorphous powder having an iron content of 21.35% weight/weight (measured complexometrically), Molecular weight mw 170 kDa.

Comparative Test

In the following, the characteristics of the iron carbohydrate complexes are compared with a commercially available iron sucrose complex. It can be seen that the iron content can be enhanced, the thermal treatment can be carried out at higher temperatures and the toxicity ($LD_{50}$) can be lowered in accordance with the invention.

|  | According to the invention | Iron hydroxide/sucrose |
|---|---|---|
| Fe content [%] | 5.0 | 2.0 |
| pH | 5-7 | 10.5-11.0 |
| mw [kDa][1] | 80-350 | 34-54 |
| Thermal treatment | 121° C./15' | 100° C./35' |
| $LD_{50}$ i.v., w.m. [mg Fe/kg body weight] | >2000 | >200 |

The invention claimed is:

1. An iron (III) carbohydrate complex comprising at least one oxidized maltodextrin and the weight average molecular weight of the iron (III) carbohydrate complex is 80 kDa to 400 kDa, wherein said at least one maltodextrin prior to oxidation has a dextrose equivalent between 5 and 20, and when a mixture of several maltodextrins is applied, the dextrose equivalent is between 5 and 20 and the dextrose equivalent of each individual maltodextrin contained in the mixture is between 2 and 40.

2. The iron (III) carbohydrate complex of claim 1, wherein 80% to 100% of one aldehyde group per molecule of maltodextrin are oxidized.

3. The iron (III) carbohydrate complex of claim 1, wherein the oxidized maltodextrin is obtained by oxidation of maltodextrin in an aqueous hypochlorite solution.

4. The iron (III) carbohydrate complex of claim 1 suitable for administration as therapy or prophylaxis for an iron deficiency condition.

5. The iron (III) carbohydrate complex of claim 1 suitable for parenteral administration as a medicament to an animal in need thereof.

6. The iron (III) carbohydrate complex of claim 1 suitable for parenteral administration as a medicament to an animal in need thereof in the form of a single dose of 500 mg to 1000 mg iron.

7. The iron (III) carbohydrate complex of claim 1 in the form of a powder.

8. An aqueous solution of the iron (III) carbohydrate complex of claim 1.

9. The aqueous solution of the iron (III) carbohydrate complex of claim 8 suitable for intravenous administration as a medicament to an animal in need thereof.

10. The aqueous solution of the iron (III) carbohydrate complex of claim 8 having an iron content of 1% weight/volume of the solution to 20% weight/volume of the solution.

11. The aqueous solution of the iron (III) carbohydrate complex of claim 9 having an iron content of 1% weight/volume of the solution to 20% weight/volume of the solution.

12. The aqueous solution of the iron (III) carbohydrate complex of claim 8 that has been sterilized at a temperature of at least 121° C.

13. The aqueous solution of the iron (III) carbohydrate complex of claim 10 that has been sterilized at a temperature of at least 121° C.

14. The aqueous solution of the iron (III) carbohydrate complex of claim 11 that has been sterilized at a temperature of at least 121° C.

15. The aqueous solution of the iron (III) carbohydrate complex of claim 8 that is free of preservatives.

16. The aqueous solution of the iron (III) carbohydrate complex of claim 10 that is free of preservatives.

17. The aqueous solution of the iron (III) carbohydrate complex of claim 11 that is free of preservatives.

18. The aqueous solution of the iron (III) carbohydrate complex of claim 14 that is free of preservatives.

19. An iron (III) carbohydrate complex comprising at least one oxidized maltodextrin and the weight average molecular weight of the iron (III) carbohydrate complex is 118 kDa to 400 kDa, wherein said at least one maltodextrin prior to oxidation has a dextrose equivalent between 5 and 20, and when a mixture of several maltodextrins is applied, the dextrose equivalent is between 5 and 20 and the dextrose equivalent of each individual maltodextrin contained in the mixture is between 2 and 40.

20. The iron (III) carbohydrate complex of claim 19, wherein 80% to 100% of one aldehyde group per molecule of maltodextrin are oxidized.

21. The iron (III) carbohydrate complex of claim 19, wherein the oxidized maltodextrin is obtained by oxidation of maltodextrin in an aqueous hypochlorite solution.

22. The iron (III) carbohydrate complex of claim 19 suitable for administration as therapy or prophylaxis for an iron deficiency condition.

23. The iron (III) carbohydrate complex of claim 19 suitable for parenteral administration as a medicament to an animal in need thereof.

24. The iron (III) carbohydrate complex of claim 19 suitable for parenteral administration as a medicament to an animal in need thereof in the form of a single dose of 500 mg to 1000 mg iron.

25. The iron (III) carbohydrate complex of claim 19 in the form of a powder.

26. An aqueous solution of the iron (III) carbohydrate complex of claim 19.

27. The aqueous solution of the iron (III) carbohydrate complex of claim 26 suitable for intravenous administration as a medicament to an animal in need thereof.

28. The aqueous solution of the iron (III) carbohydrate complex of claim 26 having an iron content of 1% weight/volume of the solution to 20% weight/volume of the solution.

29. The aqueous solution of the iron (III) carbohydrate complex of claim 27 having an iron content of 1% weight/volume of the solution to 20% weight/volume of the solution.

30. The aqueous solution of the iron (III) carbohydrate complex of claim 26 that has been sterilized at a temperature of at least 121° C.

31. The aqueous solution of the iron (III) carbohydrate complex of claim 28 that has been sterilized at a temperature of at least 121° C.

32. The aqueous solution of the iron (III) carbohydrate complex of claim 29 that has been sterilized at a temperature of at least 121° C.

33. The aqueous solution of the iron (III) carbohydrate complex of claim 26 that is free of preservatives.

34. The aqueous solution of the iron (III) carbohydrate complex of claim 28 that is free of preservatives.

35. The aqueous solution of the iron (III) carbohydrate complex of claim 29 that is free of preservatives.

36. The aqueous solution of the iron (III) carbohydrate complex of claim 32 that is free of preservatives.

* * * * *